US009301744B2

(12) United States Patent
White et al.

(10) Patent No.: US 9,301,744 B2
(45) Date of Patent: *Apr. 5, 2016

(54) INDEPENDENT SUTURE TENSIONING AND SNARING APPARATUS

(71) Applicant: ArthroCare Corporation, Austin, TX (US)

(72) Inventors: George W. White, Corona, CA (US); David Gregoire, Mission Viejo, CA (US); David Aldridge, Laguna Hills, CA (US); Edward E. Dolendo, Mission Viejo, CA (US); Emil Karapetian, Costa Mesa, CA (US); Norman S. Gordon, Irvine, CA (US); Tri Nguyen, Garden Grove, CA (US)

(73) Assignee: ArthroCare Corporation, Austin, TX (US)

(*) Notice: Subject to any disclaimer, the term of this patent is extended or adjusted under 35 U.S.C. 154(b) by 72 days.

This patent is subject to a terminal disclaimer.

(21) Appl. No.: 14/448,707

(22) Filed: Jul. 31, 2014

(65) Prior Publication Data
US 2014/0364876 A1 Dec. 11, 2014

Related U.S. Application Data

(62) Division of application No. 12/487,338, filed on Jun. 18, 2009, now Pat. No. 8,828,029.

(60) Provisional application No. 61/076,795, filed on Jun. 30, 2008.

(51) Int. Cl.
A61B 17/04 (2006.01)
A61B 17/88 (2006.01)
A61B 17/06 (2006.01)
A61B 17/00 (2006.01)

(52) U.S. Cl.
CPC ............ *A61B 17/04* (2013.01); *A61B 17/0401* (2013.01); *A61B 17/0485* (2013.01); *A61B 17/06166* (2013.01); *A61B 17/8869* (2013.01); *A61B 17/0482* (2013.01); *A61B 2017/00296* (2013.01); *A61B 2017/042* (2013.01); *A61B 2017/0409* (2013.01); *A61B 2017/0456* (2013.01); *A61B 2017/0464* (2013.01); *A61B 2017/0496* (2013.01)

(58) Field of Classification Search
CPC .................. A61B 17/0401; A61B 2017/0409; A61B 2017/0496; A61B 17/0469
USPC .......................................... 606/139, 144, 232
See application file for complete search history.

(56) References Cited

U.S. PATENT DOCUMENTS

2008/0275469 A1* 11/2008 Fanton et al. ................. 606/139

* cited by examiner

Primary Examiner — Katherine M Shi

(57) ABSTRACT

In repairing soft tissue with a bone anchoring instrument (such as reattaching a tendon of a torn rotator cuff), the bone anchoring instrument may be used to anchor the soft tissue to a region of bone. The anchors inserted into the underlying bone may have one or more lengths of suture or wire attached thereto which may be tensioned independently of one another to affix the soft tissue to the bone by having a selector mechanism selectively engage and disengage ratcheted tensioning wheels from one another. Suture loading mechanisms may be employed for passing suture lengths into and/or through the anchors prior to deployment into the bone where such mechanisms may employ suture snares which are configured to reconfigure from an expanded shape through which suture lengths may be easily passed to a low-profile shape which secures the suture lengths within the snare.

6 Claims, 19 Drawing Sheets

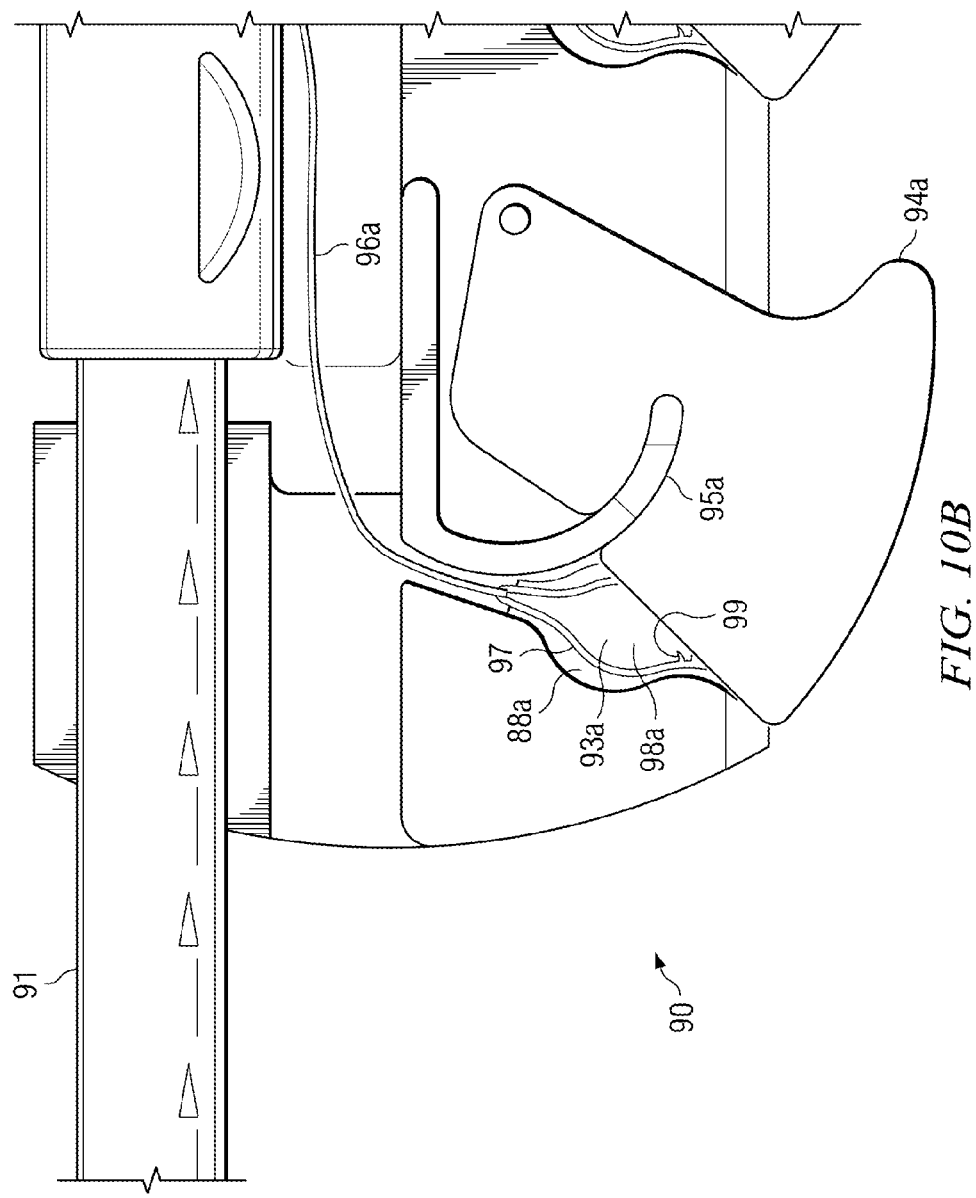

INDEPENDENT SUTURE TENSIONING AND SNARING APPARATUS

CROSS-REFERENCE TO RELATED APPLICATIONS

This application is a divisional of U.S. patent application Ser. No. 12/487,338 filed Jun. 18, 2009, which claims the benefit of U.S. Provisional Application No. 61/076,795 filed Jun. 30, 2008 and entitled "Independent Suture Tensioning and Snaring Apparatus", the entirety of which is incorporated herein by reference in its entirety.

FIELD OF THE INVENTION

The present invention relates to apparatus and methods for anchoring soft tissue to bone. More particularly, the present invention relates to apparatus and methods for anchoring soft tissue to bone and selectively snaring, threading, and tensioning varying suture lengths from one or more bone anchors independently of one another through a single instrument.

BACKGROUND OF THE INVENTION

Prior to the development of knotless designs, bone anchor deployment instruments typically utilized anchors which had suture material either preloaded or incorporated eyelets through which a length of suture may be loaded prior to anchor introduction into the bone. The sequence of operation for deploying the anchors generally entailed passing one or more suture lengths through the soft tissue to be secured and then approximating the soft tissue to the underlying bone by tying one or more knots.

Even with the advent of knotless bone anchor designs, the ability to accurately and reliably apply tension to the sutures to approximate soft tissues to bone created additional problems. Because of the nature of knotless anchor designs, sutures are typically placed through the soft tissue to be secured before coupling them with the anchor. This required the inclusion of additional mechanisms for threading the anchors and tensioning the sutures.

Developments in constructs for approximating and securing soft tissue to bone, notably in the area of rotator cuff repair, have created the need to be able to independently secure, thread, and tension one or more of the suture strands passing through one or more bone anchors. This is typically apparent in the formation of crossed suture configurations, e.g., criss-cross type constructs, where suture limbs from two different medially placed anchors are loaded into a laterally placed anchor. Because the suture limbs may originate from different orientations or bone anchors, they may not have the same lengths and may thus need to be tensioned independently of one another.

Additionally, in certain of the bone anchor insertion instrument configurations described above, there exists a need to secure suture limbs after they have been loaded into a threading or snaring device to prevent the separate suture limbs from dropping out of the insertion device. As the sutures are withdrawn over a distance through the anchor and into the inserter, the potential for the sutures pulling out of the snare and the insertion device is significant.

Accordingly, devices and methods which allow for the tensioning of separate suture lengths independently of one another are desired. In particular, mechanisms to individually capture suture lengths and convey them to tensioning mechanisms, e.g., ratchet wheels, which are controllable to enable a user to selectively tension either or both individual suture lengths are desired. Further, a suture threading and snaring device that allows for single step loading and securing of independent suture limbs into knotless bone anchors is also desired. In particular, mechanisms that allow for the individual snaring and securing of suture limbs in conjunction with the use of a bone anchor insertion device with independent tensioning mechanisms, and that convey the independent suture limbs to the separate tensioning mechanisms, e.g., ratchet wheels, are also needed

SUMMARY OF THE INVENTION

In repairing soft tissue with a bone anchoring instrument (such as reattaching a tendon of a torn rotator cuff), the bone anchoring instrument may be used to anchor the soft tissue to a region of bone. This may be accomplished generally by inserting at least one anchor into underlying bone, locking the anchor into the bone, and subsequently tensioning one or more lengths of suture or wire between the anchor to affix the soft tissue. The lengths of suture or wire may be tensioned independently of one another and subsequently immobilized or secured and the anchoring instrument may be disassociated from the anchors leaving them behind in the bone.

The suture tensioning mechanism may incorporate one or more rotatable wheels which are ratcheted to turn in a stepped or controlled manner in a first direction unless released by a ratchet release mechanism to allow for the ratcheted wheels to turn in a second opposite direction. One or more knobs may be rotatably attached to the one or more ratcheted wheels to provide a control handle for the user. Once the bone anchor has been deployed, the user may turn the one or more knobs in the first direction to tension the suture about the ratcheted wheel and thus approximate the soft tissue to the underlying bone.

Respective first and second knobs may extend from the instrument housing while coupled to respective first and second ratchet wheels which are rotatably positioned within the housing. First and second ratchet wheels may include respective ratcheting teeth such that rotation of the first and second knobs by the user may in turn rotate ratchet wheels in a first direction while rotation in a second opposite direction is inhibited. One or both respective ratchet releases may be depressed or actuated by the user to release the ratcheting mechanism and thus allow for free rotation of the ratchet wheels in either the first or second direction. In this manner, one or both ratchet wheels may be released independently of one another to facilitate individual tensioning of one or both suture lengths via the ratchet wheels. Alternatively, both ratchet wheels may be simultaneously released by the simultaneous actuation of both ratchet releases.

In an exemplary use, when a first and second length of suture extending from their respective bone anchors deployed within the underlying bone are initially tensioned, the selector may be placed in a neutral position such that both first and second ratchet wheels are engaged by the selector and both wheels are simultaneously rotatable. Rotation of both first and second ratchet wheels may accordingly tension both lengths of suture simultaneously about their respective suture tracks for initially eliminating any slack from the suture lengths.

To disengage the first and second ratchet wheels from one another, the selector may be actuated, e.g., by depressing the selector in a first direction, to slide into a first position. In this first position, the second ratchet wheel may be disengaged and the first ratchet wheel may be engaged such that rotation of the knobs may in turn rotate only the first ratchet wheel to tension the first length of suture thereabout. With the second ratchet wheel disengaged from the knobs, the second ratchet wheel may remain stationary to maintain a constant tension level upon its suture length while the first ratchet wheel may be rotated to further tension or loosen its first length of suture as appropriate. Similarly, the selector may be actuated to be re-positioned into a second position where the first ratchet wheel is disengaged from the knobs and the second ratchet wheel is then engaged by the knobs to rotate for tensioning or loosening its respective suture length. Such individual tensioning of the sutures may provide for fine tuning and optimization of the soft tissue securement to the underlying bone.

As the selector is moved between positions during a procedure, a retaining member located along the selector shaft may slide over an interface between the ratchet wheels to an provide an indication, such as slight resistance or an audible click, to the user as to the relative movement and positioning of the selector relative to the ratchet wheels.

Prior to tensioning the lengths of suture, a suture loader comprising a snaring and securing mechanism is provided to assist in conveying the separate suture limbs to a respective independent tensioning ratchet wheel. The snaring mechanism includes at least two snares preloaded into the suture loader. The securing mechanism includes a suture guide disposed on the inserter. The suture guide manages and effectively routes each snare and corresponding length of suture limbs from an initial snaring position to a subsequent pre-tensioning position where each length of suture limb is drawn through the bone anchor prior to the tensioning process. The securing mechanism further includes at least two traps and related shutters that may be movable either pivotably or slidably and operable to capture suture limbs disposed in a corresponding snare in the initial snaring position within the traps and prior to the suture limbs being withdrawn through a bone anchor by the tensioning mechanism. The suture limbs are engaged by at least two snare end portions that each comprise a plurality of teeth for engaging, compressing into, or biting into the end portions of the respective suture limbs.

Thus, the disclosed embodiments comprise a combination of features and characteristics which are directed to allow it to overcome various shortcomings of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

FIGS. 10A, 10B, and 10C illustrate perspective views of an embodiment of the removable suture loader disposed at a distal end of a bone anchoring instrument.

DETAILED DESCRIPTION OF THE INVENTION

The independent suture tensioning mechanisms described herein may be utilized with any number of bone anchors as well as related insertion and deployment instruments. In repairing soft tissue with a bone anchoring instrument (such as reattaching a tendon of a torn rotator cuff), the bone anchoring instrument may be used to anchor the soft tissue to a region of bone. This may be accomplished generally by inserting at least one anchor into the underlying bone, locking the anchor into the bone, and subsequently tensioning one or more lengths of suture or wire stitched in the soft tissue between the anchor to affix the soft tissue. The lengths of suture or wire may be tensioned independently of one another and subsequently immobilized or secured and the anchoring instrument may be disassociated from the anchor leaving it behind in the bone. Such an anchoring instrument may eliminate the need to separately pass suture or wire or tying knots thus allowing the procedure to be performed without the need to move an arthroscope from an articular side to a bursal side of the cuff. Moreover, the relatively small diameter of the bone anchor allows for a reduced entry hole through the cuff during delivery and deployment.

Some examples of illustrative bone anchoring devices which may incorporate such suture tensioning mechanisms are shown and described in detail in U.S. Pat. No. 6,780,198 and U.S. Pat. App. 2005/033364 A1, each of which is incorporated herein by reference. Generally, such bone anchor deployment instruments may incorporate one or more ratcheted tensioning mechanisms, such as a rotatable wheel, around which a length of suture to be deployed and tensioned is at least partially wrapped or retained. Once the anchor has been deployed into the bone and the suture extending from the anchor is to be tensioned, the tensioning mechanism may be rotated in a first direction (as in the wheel configuration) to wind the slack suture about the mechanism and thereby apply tension to the suture ends, e.g., to approximate and/or secure soft tissue to the bone.

Figure 1:
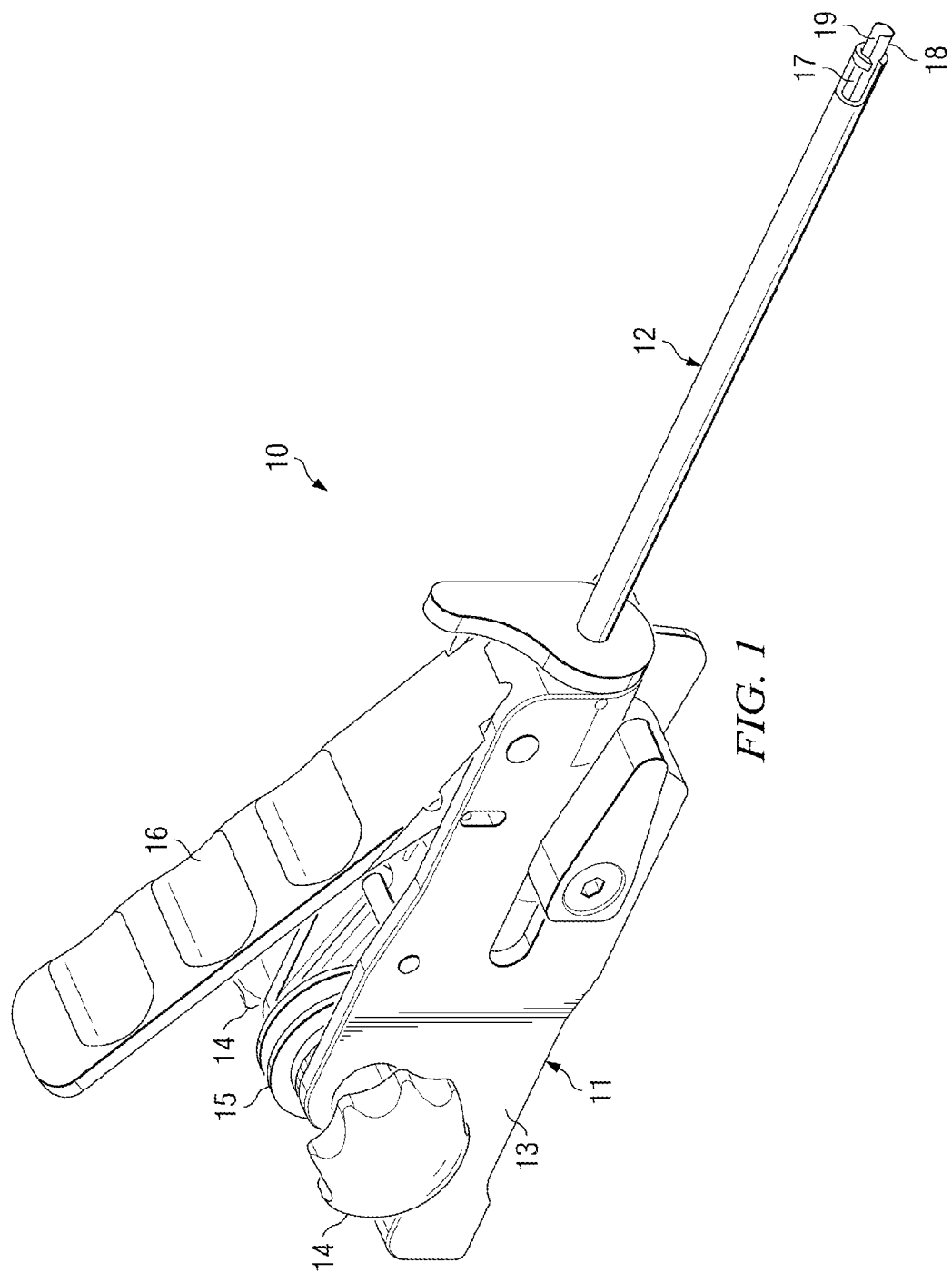
FIG. 1 illustrates a perspective view of a representative bone anchoring instrument.

One embodiment of a bone anchoring insertion instrument having a ratcheted tensioning mechanism configured as a rotatable wheel is shown in the perspective view of FIG. 1. As previously mentioned, further details are disclosed in U.S. Pat. No. 6,780,198 and U.S. Pat. App. 2005/033364 A1 incorporated hereinabove. A bone anchoring insertion instrument 10 may incorporate an inserter handle 11 and an outer tube 12 extending distally from handle portion 11. The handle portion 11 may comprise a housing 13 which is shaped and configured to accommodate components for effecting the insertion of one or more bone anchors for any number of orthopedic procedures such as repair of a rotator cuff where a portion of soft tissue is reattached to an adjacent bone. A hand lever 16 may be pivotally attached to housing 13.

The suture tensioning mechanism may incorporate a rotatable wheel 15 which is ratcheted to turn in a stepped or controlled manner in a first direction unless released by a ratchet release mechanism to allow for the ratcheted wheel 15 to turn in a second opposite direction. One or more knobs 14 may be rotatably attached to the one or more ratcheted wheels 15 to provide a control handle for the user. The bone anchor may be deployed by actuating the pivotable hand lever 16 downwardly. Once the bone anchor has been deployed, the user may turn the one or more knobs 14 in the first direction to tension the suture about the ratcheted wheel 15 and thus approximate the soft tissue to the underlying bone.

The outer tube 12 projecting distally from handle 11 may define a longitudinal slot or opening 19 as well as a suture opening 17 formed in its distal end. A separate inner slotted tube 18 may also be disposed coaxially within the outer tube 12 such that inner tube 18 is fixed relative to the outer tube 12 to prevent relative sliding or rotational movement between the two. In this manner, inner tube 18 may function as a mandrel or stop for the bone anchors during an insertion procedure.

Figure 2:
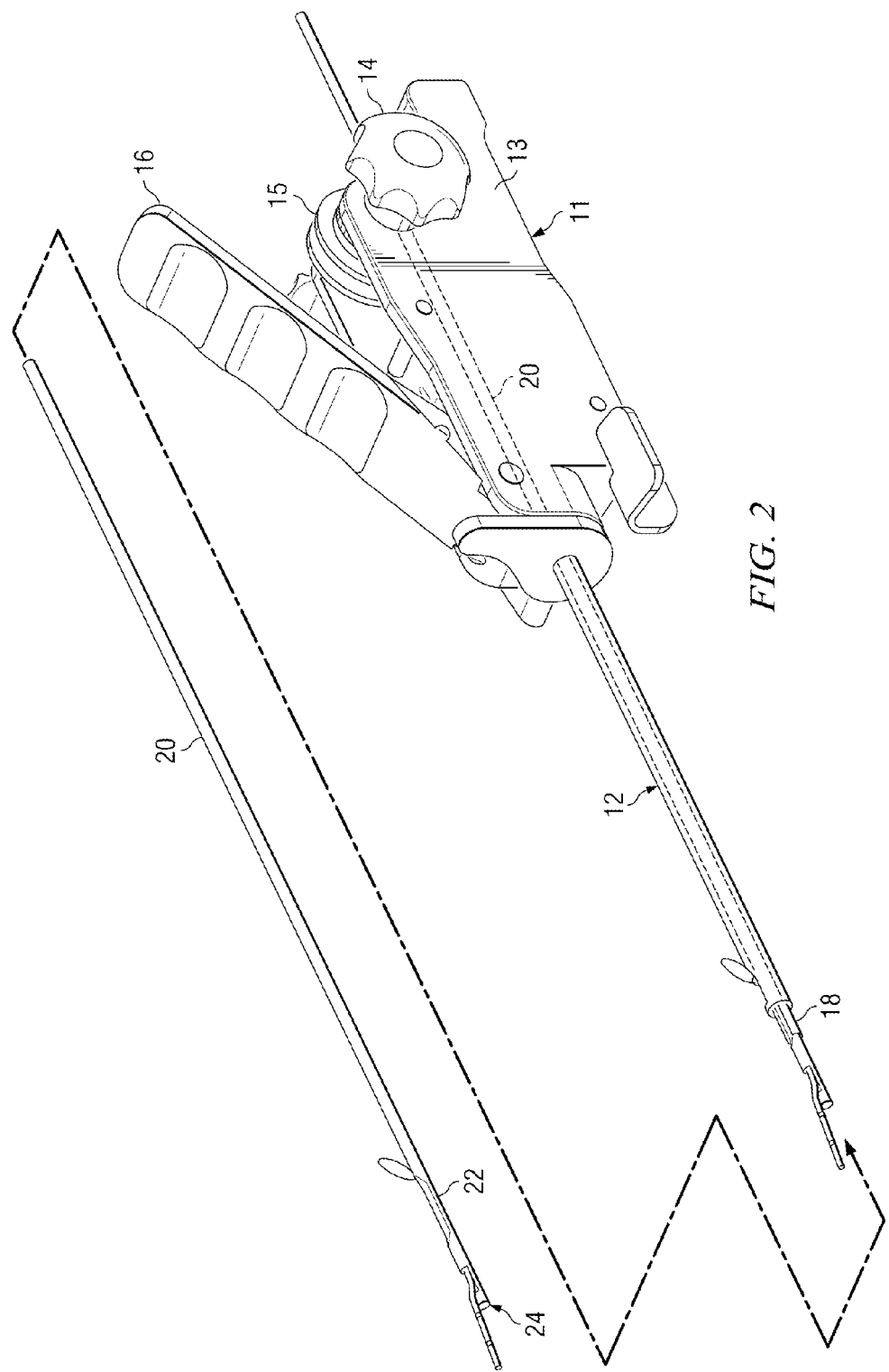
FIG. 2 illustrates another perspective view of an a representative bone anchoring assembly which shows the deployable bone anchors which may be loaded within the instrument.

As illustrated in the perspective view of FIG. 2, a separate pull tube 20 may also be inserted in a coaxial relationship into the distal end of the inner slotted tube 18. A portion of the distal end of the pull tube 20 may be constructed such that part of the cylindrical sidewall is cut away to form a semi-cylindrical shape which forms a suture opening 22. In this manner, one or more bone anchors 24 to which a length of suture is attached may be affixed to the distal end of pull tube 20 for delivery and deployment into the bone.

Figure 3:
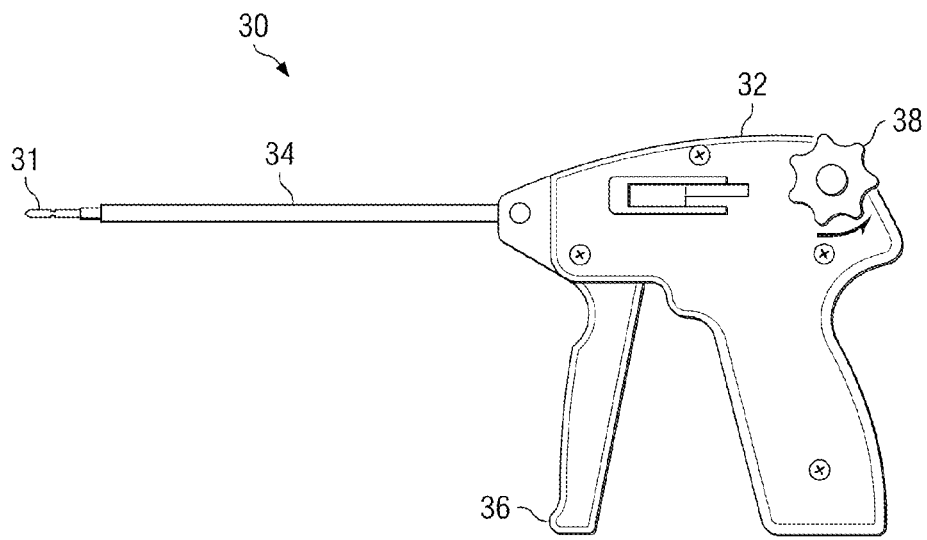
FIG. 3 illustrates a perspective view of an additional bone anchoring instrument.

Referring now to FIG. 3, another embodiment of a bone anchoring insertion instrument is shown. Bone anchor insertion device 30 is comprised of handle 32, outer tube 34, and trigger 36. Suture knob 38 is disposed on handle 32, and is rotatably attached to a ratcheted wheel (not shown). Bone anchor 31 is disposed at a distal end of outer tube 34 and is threaded with a length of suture (not shown) which is also retained on the ratcheted wheel. The bone anchor 31 is inserted into a bone hole and the length of suture is tensioned by rotating suture knob 38. After the length of suture is tensioned to a desired degree, trigger 36 is actuated in order to deploy and lock the bone anchor 31 within the bone hole.

Figure 4:
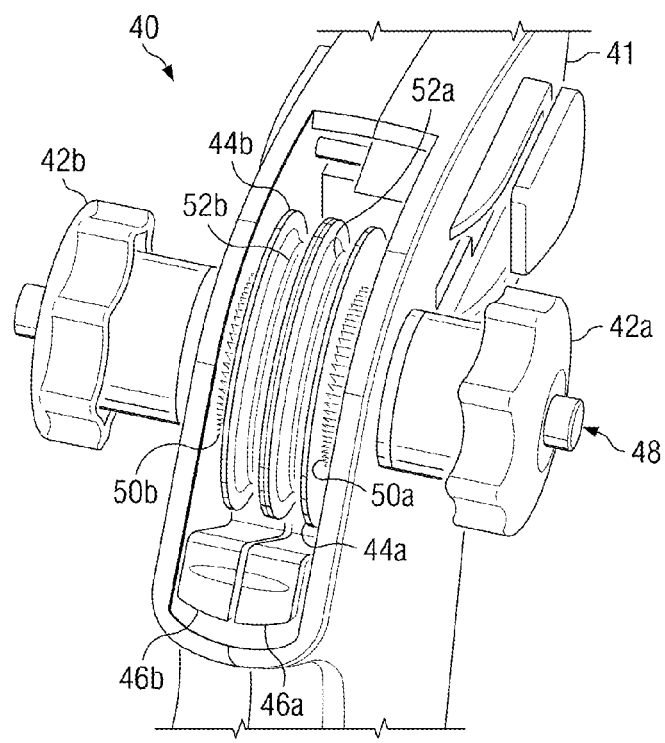
FIG. 4 illustrates a perspective view of one example of a suture tensioning assembly configured to simultaneously tension two separate suture lengths.

The bone anchoring insertion instruments shown above are described as exemplary devices which may incorporate a suture tensioning mechanism configured to tension different suture lengths simultaneously or independently of one another and are not intended to be limiting. Now turning to an example of such a suture tensioning mechanism, FIG. 4 illustrates a perspective view of a suture tensioning mechanism 40 housed within handle housing 41. In this variation, respective first and second knobs 42a, 42b may extend from housing 41 while coupled to respective first and second ratchet wheels 44a, 44b which are rotatably positioned within housing 41. First and second ratchet wheels 44a, 44b may include respective ratcheting teeth 50a, 50b such that rotation of the first and second knobs 42a, 42b by the user may in turn rotate ratchet wheels 44a, 44b in a first direction while rotation in a second opposite direction is inhibited.

One or both respective ratchet releases 46a, 46b may be depressed or actuated by the user to release the ratcheting mechanism and thus allow for free rotation of ratchet wheels 44a, 44b in either the first or second direction. For instance, actuation of first ratchet release 46a may release the ratcheting mechanism from ratcheting teeth 50a and actuation of second ratchet release 46b may release the ratcheting mechanism from ratcheting teeth 50b. In this manner, one or both ratchet wheels 44a, 44b may be released independently of one another to facilitate individual tensioning of one or both suture lengths via ratchet wheels 44a, 44b, as further described below. Alternatively, both ratchet wheels 44a, 44b may be simultaneously released by the simultaneous actuation of both ratchet releases 46a, 46b. Furthermore as shown, first and second ratchet wheels 44a, 44b may each define a groove or track 52a, 52b about its circumference within which respective lengths of suture to be tensioned may be at least partially wrapped about.

In an exemplary use, when a first and second length of suture extending from their respective bone anchors deployed within the underlying bone are initially tensioned, selector 48 may be placed in a neutral position, as shown in FIG. 4, such that both first and second ratchet wheels 44a, 44b are engaged by selector 48 and both wheels are simultaneously rotatable by first and second knobs 42a, 42b. Rotation of both first and second ratchet wheels 44a, 44b may accordingly tension both lengths of suture simultaneously about their respective suture tracks 52a, 52b for initially eliminating any slack from the suture lengths.

Figure 5A:
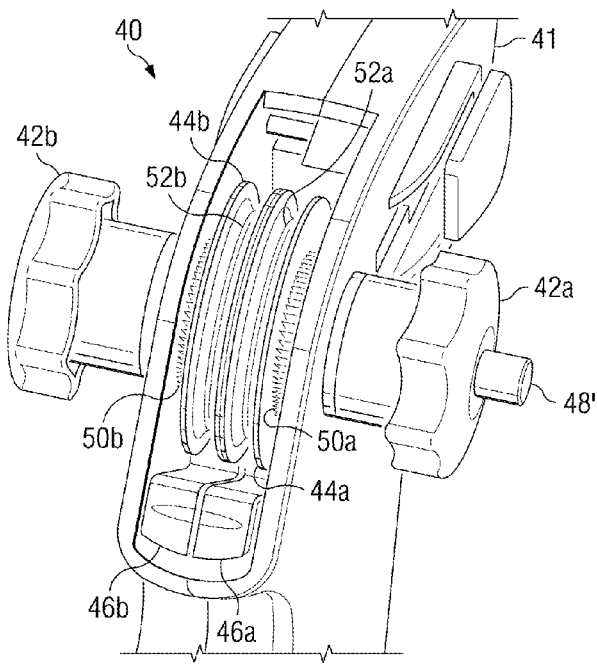
FIGS. 5A and 5B illustrate perspective views of the suture tension assembly alternately configured to selectively tension a first or a second suture length.

To disengage first and second ratchet wheels 44a, 44b from one another, selector 48 may be actuated, e.g., by depressing selector 48 in a first direction, to slide into a first position 48', as illustrated in the perspective view of FIG. 5A. In this first position 48', second ratchet wheel 44b may be disengaged and first ratchet wheel 44a may be engaged such that rotation of knobs 42a, 42b may in turn rotate only first ratchet wheel 44a to tension the first length of suture thereabout. With second ratchet wheel 44b disengaged from knobs 42a, 42b, second ratchet wheel 44b may remain stationary to maintain a constant tension level upon its suture length while first ratchet wheel 44a may be rotated to further tension or loosen its first length of suture as appropriate.

Figure 5B:
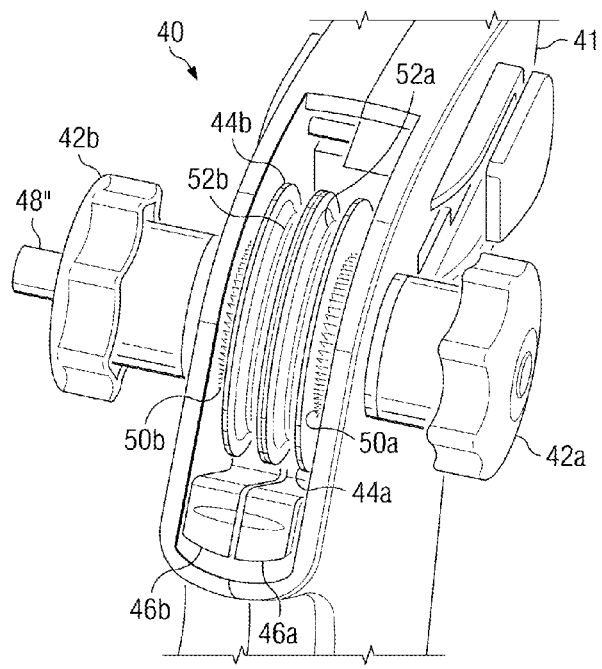

Similarly, selector 48 may be actuated to be re-positioned into a second position 48", as illustrated in the perspective view of FIG. 5B, where first ratchet wheel 44a is disengaged from knobs 42a, 42b and second ratchet wheel 44b is then engaged by the knobs to rotate for tensioning or loosening its respective suture length. Alternatively, engagement of selector 48 into its first position 48' may allow for rotation of first ratchet wheel 44a by only first knob 42a and likewise engagement of selector 48 into its second position 48" may allow for rotation of second ratchet wheel 44b by only second knob 42b. Selector 48 may be repositioned in its neutral position or its first or second position at any time during a procedure thus allowing for simultaneous tensioning or selective tensioning of its first or second suture lengths as necessary. Such individual tensioning of the sutures may provide for fine tuning and optimization of the soft tissue securement to the underlying bone.

Figure 6:
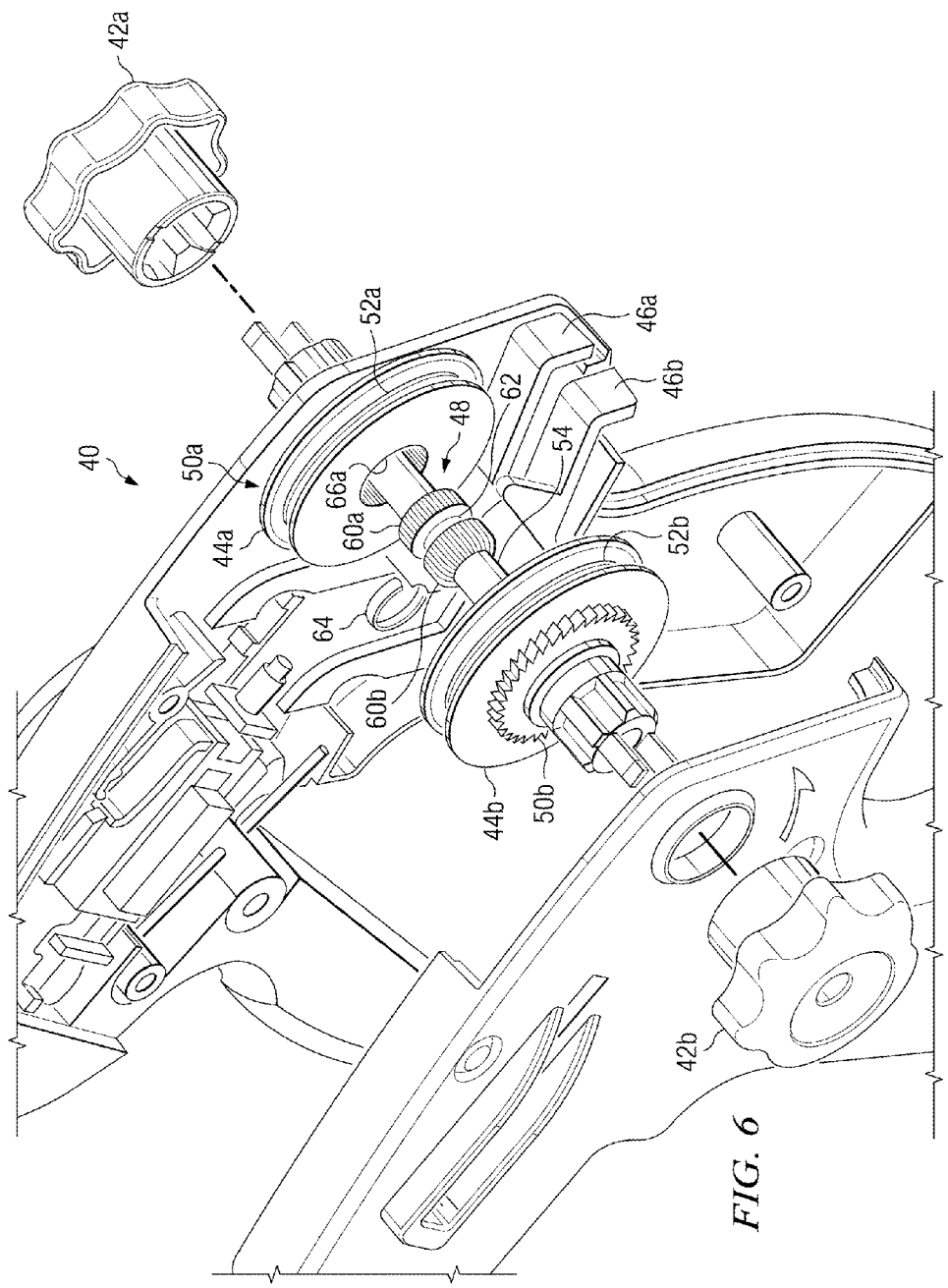
FIG. 6 illustrates a perspective view of an exploded tensioning assembly showing the separate tensioning mechanisms and a selector assembly for selectively engaging one or both tensioning mechanisms.

As illustrated in the perspective view of the exploded tensioning mechanism assembly in FIG. 6, selector 48 may comprise in one variation a shaft 54 translatable along its axial length and positioned through ratchet wheels 44a, 44b. An engagement member having first and second engaging portions 60*a*, 60*b* may be positioned along the shaft 54, e.g., along a central portion of shaft 54. The engaging portions 60*a*, 60*b* may comprise a separate or integrated portion of shaft 54 which has a second diameter larger than a first diameter of the shaft 54 with one or more teeth or projections defined along the engaging portions 60*a*, 60*b* and extending in a longitudinal direction. The engaging portions 60*a*, 60*b* may further include a receiving groove 62 circumferentially defined between engaging portions 60*a*, 60*b* such that receiving groove 62 is sized to receive a retaining member 64, e.g., C-clip or O-ring, which may be secured within receiving groove 62. Once retaining member 64 is secured within receiving groove 62, an outer diameter of the member 64 may extend just beyond the second diameter of engaging portions 60*a*, 60*b*.

First and second ratchet wheels 44*a*, 44*b* may each define a respective receiving recess 66*a*, 66*b* molded or otherwise formed annularly about the opening through which selector shaft 54 passes such that the annular cavities are in apposition to one another. Receiving recess 66*a*, 66*b* may each form an opening along the surfaces of ratchet wheels 44*a*, 44*b* such that when the wheels are positioned adjacent to one another when assembled, receiving recess 66*a*, 66*b* forms an enclosed cavity within which first and second engaging portions 60*a*, 60*b* are translatably slidable.

Figure 7A:
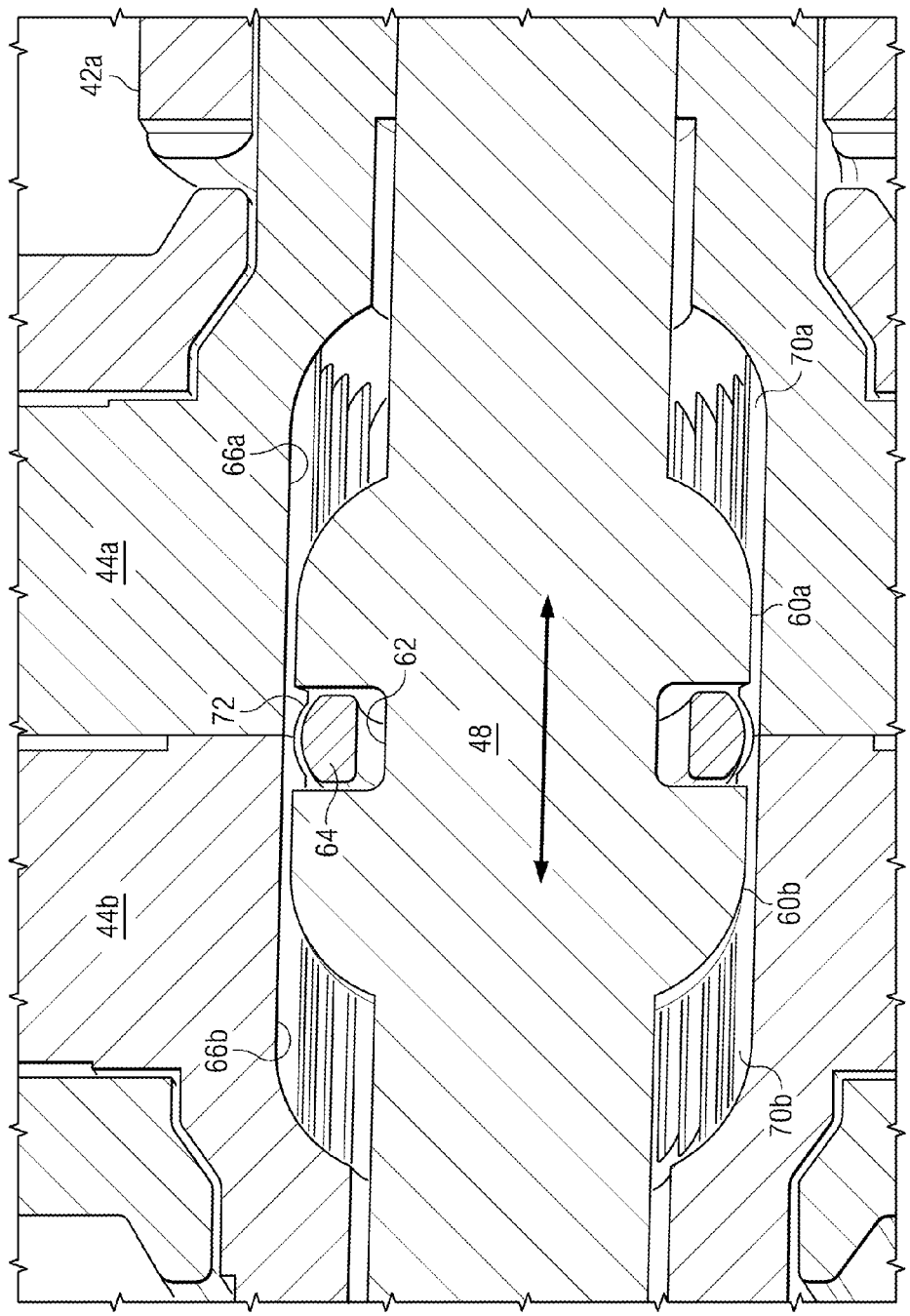
FIG. 7A illustrates a cross-sectional end view of the selector assembly in a first position to engage both a first and a second tensioning mechanism to simultaneously tension a first and a second suture length, respectively.

As illustrated in the cross-sectional end view of FIG. 7A, the assembled ratchet wheels 44*a*, 44*b* are shown positioned adjacent to one another such that the receiving recess 66*a*, 66*b* forms the enclosed cavity. The interior surface of receiving recess 66*a*, 66*b* may each define one or more engaging teeth or projections 70*a*, 70*b* which extend longitudinally therethrough such that the engaging teeth or projections defined along engaging portions 60*a*, 60*b* are received in a complementary manner where the engaging portions 60*a*, 60*b* becomes rotationally coupled to one or both ratchet wheels 44*a*, 44*b* via engagement with the interior of receiving recess 66*a*, 66*b*. Because of the longitudinal direction which the engaging teeth along engaging portions 60*a*, 60*b* and the engaging teeth 70*a*, 70*b* along the interior surface of receiving recess 66*a*, 66*b* are positioned, selector 48 may remain slidingly translatable along its longitudinal axis, as indicated by the arrow, to translate freely within receiving recess 66*a*, 66*b* while remaining in rotational engagement with one or both ratchet wheels 44*a*, 44*b*.

Figure 7B:
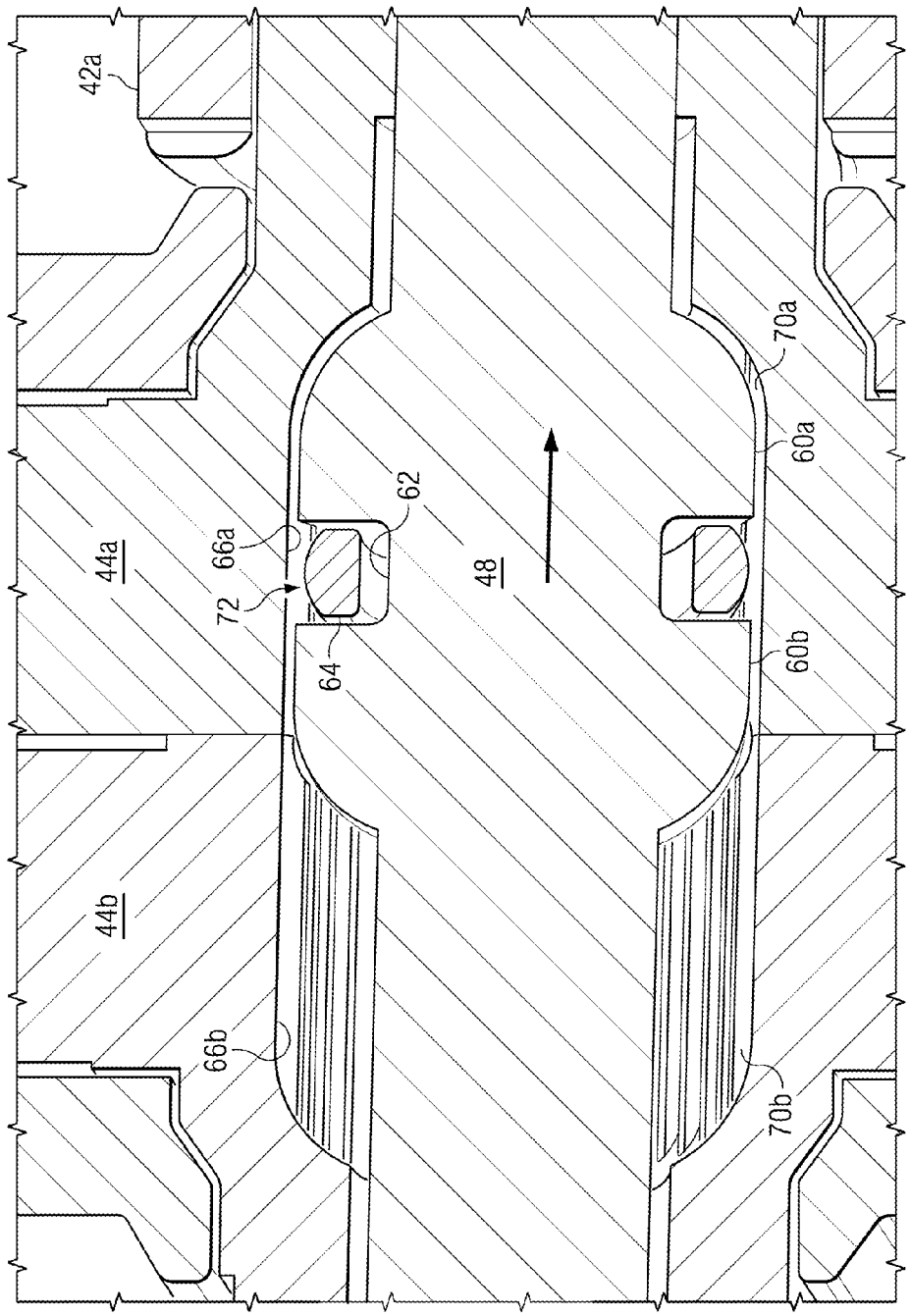
FIG. 7B illustrates the cross-sectional end view of FIG. 6A where the selector assembly is repositioned in a second position to engage a single tensioning mechanism for tensioning a single suture length.

When selector 48 is positioned in its neutral position as described above, first and second engaging portions 60*a*, 60*b* may be engaged to both first and second ratchet wheels 44*a*, 44*b*, as shown, to allow for simultaneous rotation of the wheels and tensioning of their respective suture lengths. However, upon actuation of selector 48 to its first position, as shown in the cross-sectional end view of FIG. 7B, selector 48 and engaging portions 60*a*, 60*b* may slide within receiving recess 66*a*, 66*b* such that second engaging portion 60*b* becomes disengaged from the teeth or projections along second receiving recess 66*b* and becomes engaged solely with first ratchet wheel 44*a*. In this manner, first ratchet wheel 44*a* may be actuated to selectively tension just the first length of suture. Actuating selector 48 to slide into its second position may likewise disengage first and second engaging portions 60*a*, 60*b* from first ratchet wheel 44*a* such that second ratchet wheel 44*b* becomes solely engaged for tensioning just the second length of suture. Selector 48 may be accordingly engaged and disengaged freely from either ratchet wheel to selectively tension one or both lengths of sutures during a procedure.

To facilitate the selective engagement of one or both ratchet wheels 44*a*, 44*b*, the exterior circumferential surface of retaining member 64 may remain in sliding contact 72 with the interior surface of receiving recess 66*a*, 66*b* to provide tactile feedback to the user. As selector 48 is moved between positions during a procedure, the retaining member 64 may slide over the interface between the ratchet wheels 44*a*, 44*b* and provide an indication, such as slight resistance or an audible click, to the user as to the relative movement and positioning of selector 48 relative to the ratchet wheels 44*a*, 44*b*.

Figure 8A:
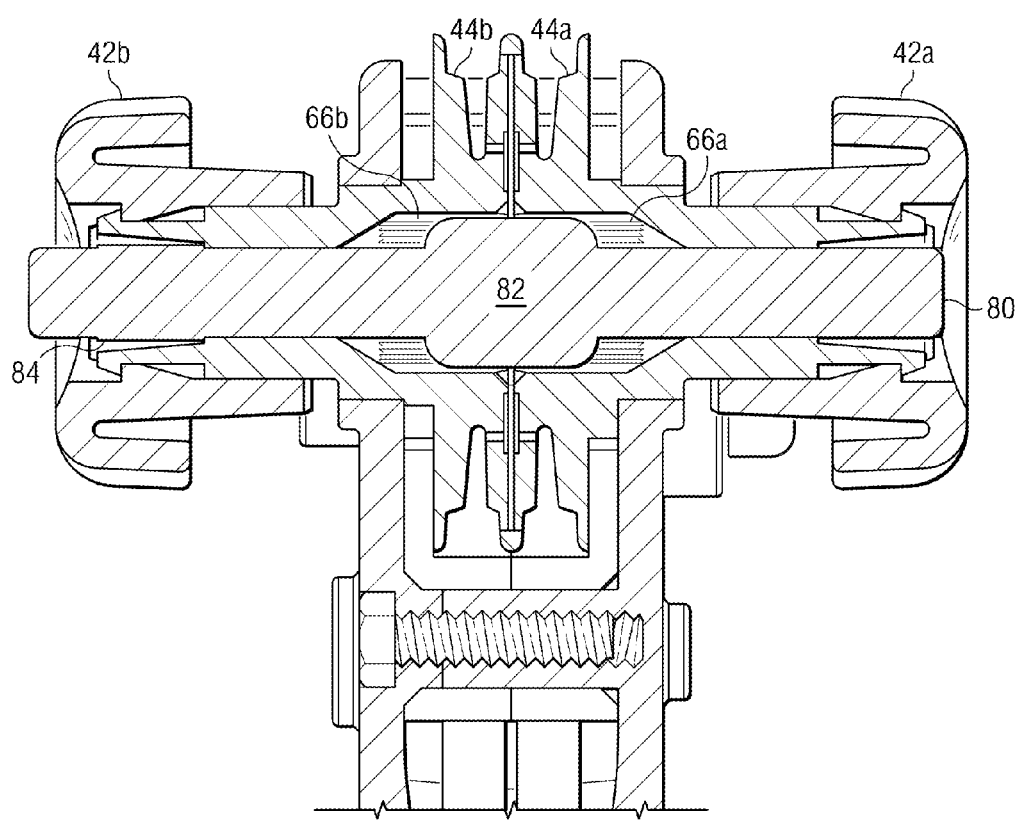
FIGS. 8A and 8B illustrate cross-sectional end views of another variation of a selector assembly which is configured to selectively engage one or both the tensioning mechanisms in preset positions.
Figure 8B:
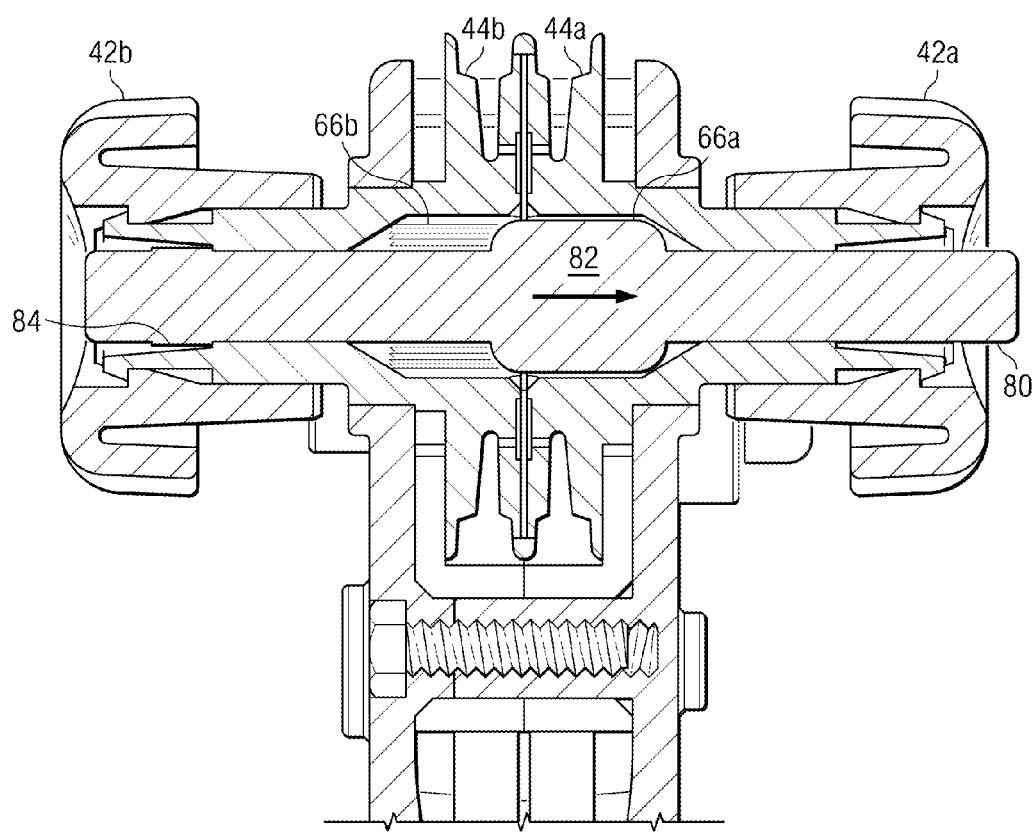

In yet another variation, FIGS. 8A and 8B illustrate cross-sectional end views of a selector 80 mechanism which is configured to toggle between one of two positions. In the end view of FIG. 8A, selector 80 may be toggled in a first position where engaging portion 82 located along the selector shaft is engaged to both first and second ratchet wheels 44*a*, 44*b* such that both wheels are coupled and actuation of knobs 42*a*, 42*b* simultaneously tensions (or loosens) each respective suture length. When selector 80 is toggled into its second position, as illustrated in FIG. 8B, ratchet wheels 44*a*, 44*b* may be uncoupled from one another to allow for individual suture tensioning as described above. In this example, a portion of selector 80 may define a keyed length 84 such that selector 80 is capable of being toggled in only one or two positions. Other variations for limiting selector position may, of course, be utilized with the tensioning mechanisms described above.

Figure 9A:
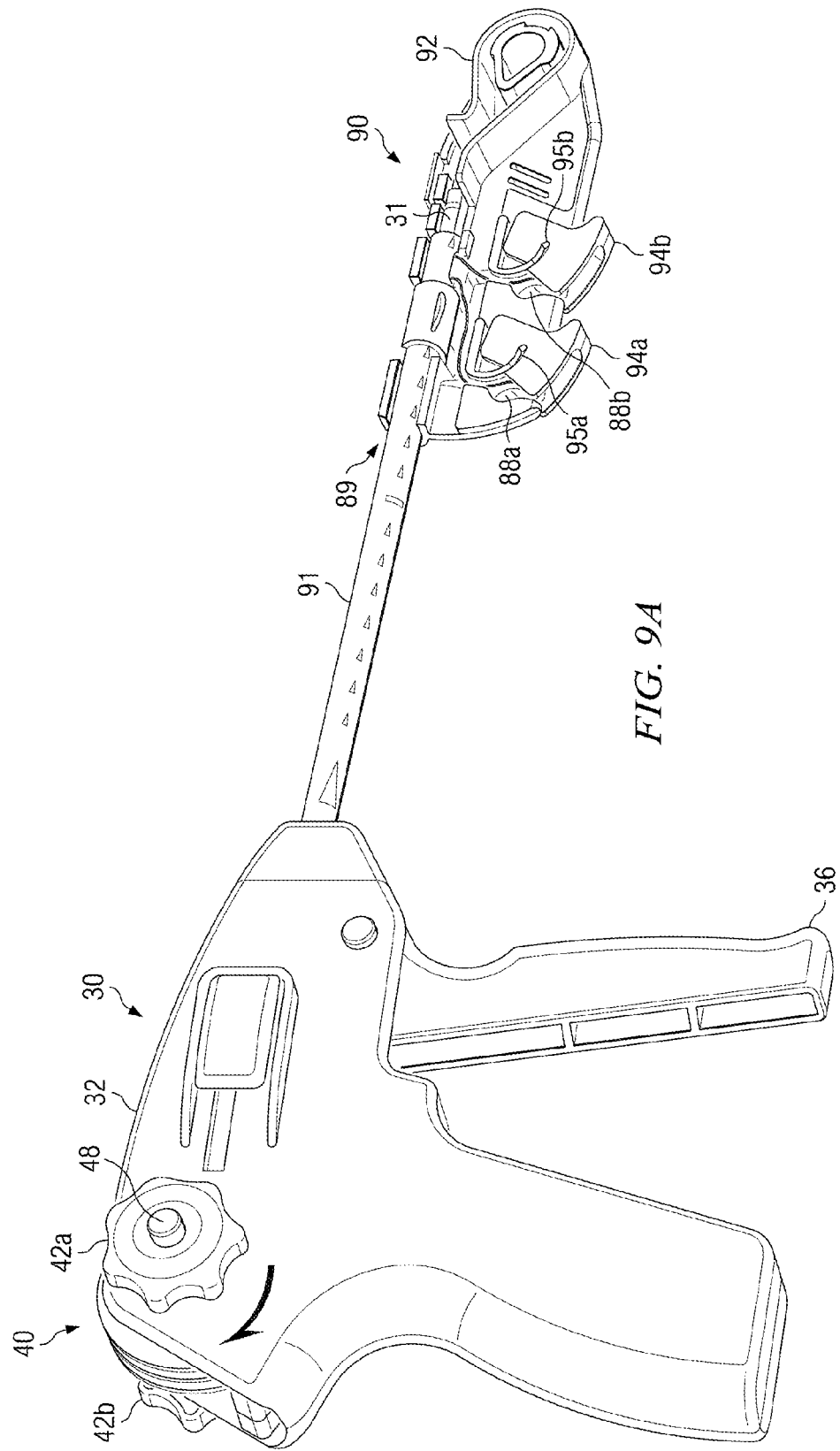
FIGS. 9A and 9B illustrate perspective and detail perspective views, respectively, of an exemplary bone anchor insertion device positioned within a suture loader mechanism.
Figure 9B:
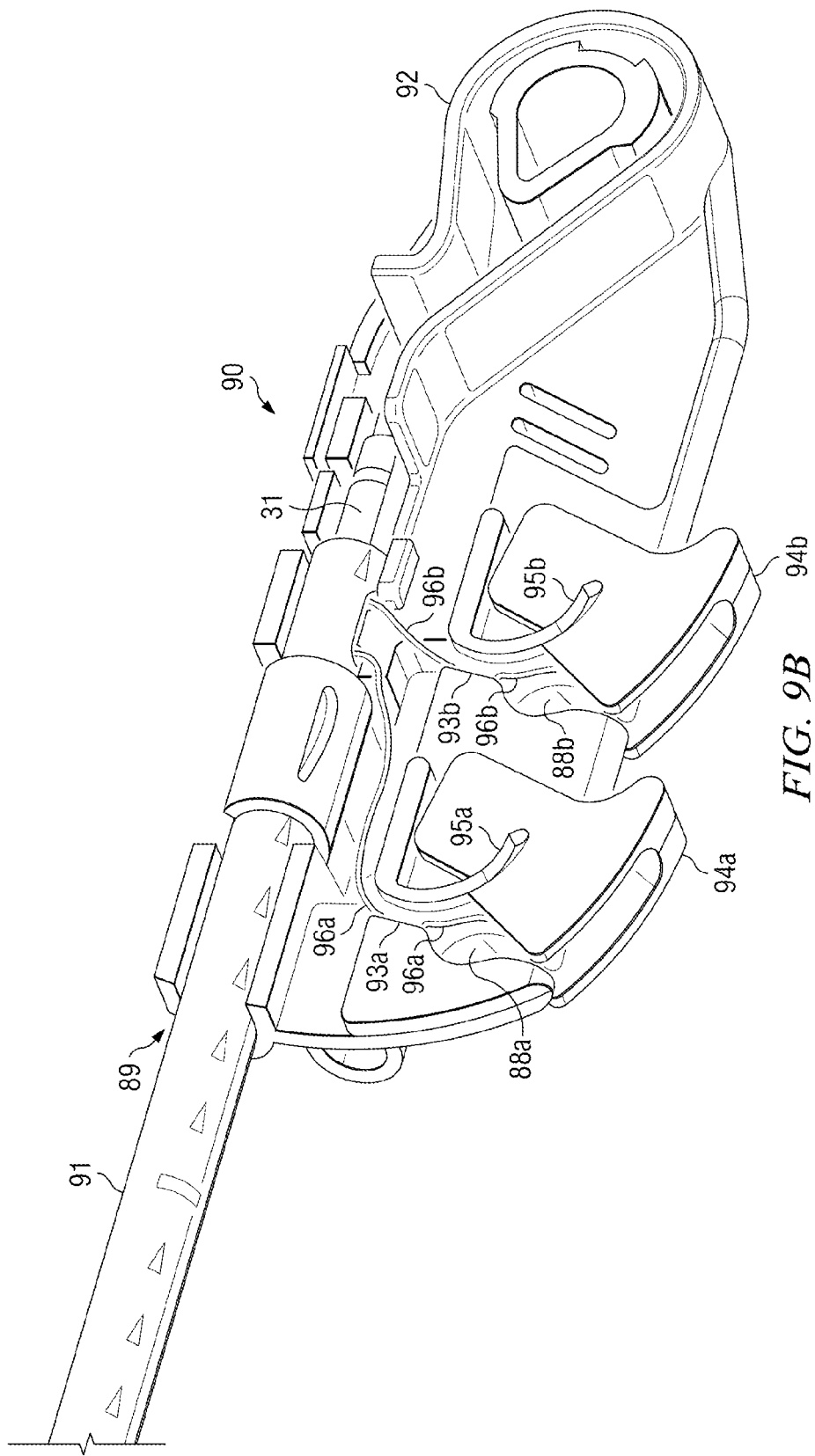

Aside from independently tensioning suture lengths after one or more bone anchors have been deployed in the bone, additional mechanisms may be optionally utilized to facilitate the passage and loading of multiple suture lengths into or through the one or more bone anchors prior to anchor deployment. One embodiment is illustrated in the perspective assembly view of FIG. 9A which shows an exemplary bone anchor insertion device 30, as previously described, having a suture loader mechanism 90 (described in further detail below) into which outer tube 91 having bone anchor 31 may be introduced. Additionally, in certain embodiments bone anchor insertion device 30 may comprise a suture tensioning mechanism 40 according to the embodiments described herein. FIG. 9B shows a detail perspective view of suture loader 90 and outer tube 91 with bone anchor 31 inserted within loader 90.

Generally, suture loader 90 may define a tube receiving channel 89 into which outer tube 91 may be slidably and removably positioned. With bone anchor 31 positioned distally of outer tube 91, one or more suture snares 96*a*, 96*b* (also described in further detail below) may be passed through the anchor 31 and through suture traps 93*a*, 93*b* having apertures 88*a*, 88*b*. Appropriate suture lengths may be passed through the one or more suture snares 96*a*, 96*b* which may be positioned within corresponding apertures 88*a*, 88*b* of traps 93*a*, 93*b* defined through loader 90. With the suture lengths positioned through apertures 98*a*, 98*b* of snares 96*a*, 96*b*, they may be secured by snares 96*a*, 96*b* and passed through anchor 31 via loader 90.

Figure 10A:
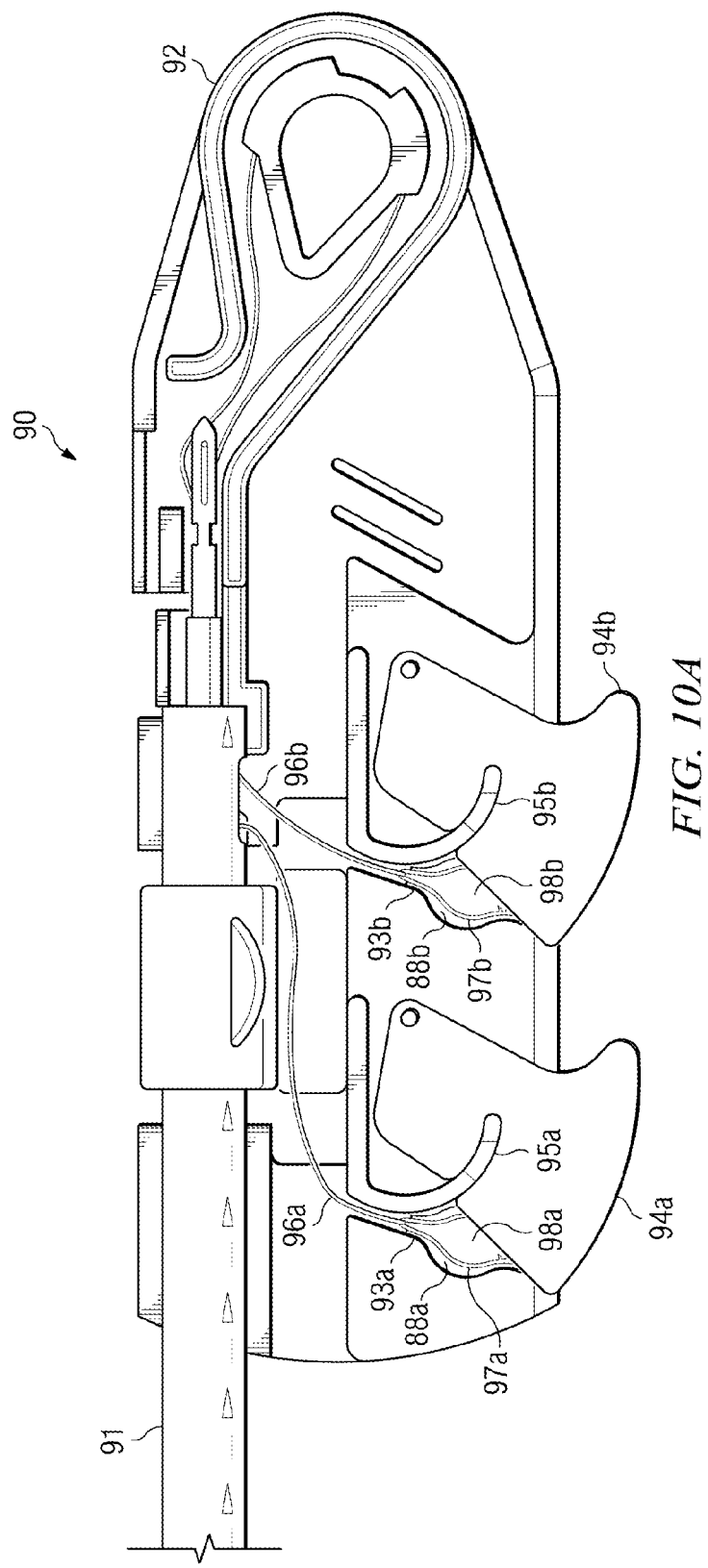
Figure 10C:
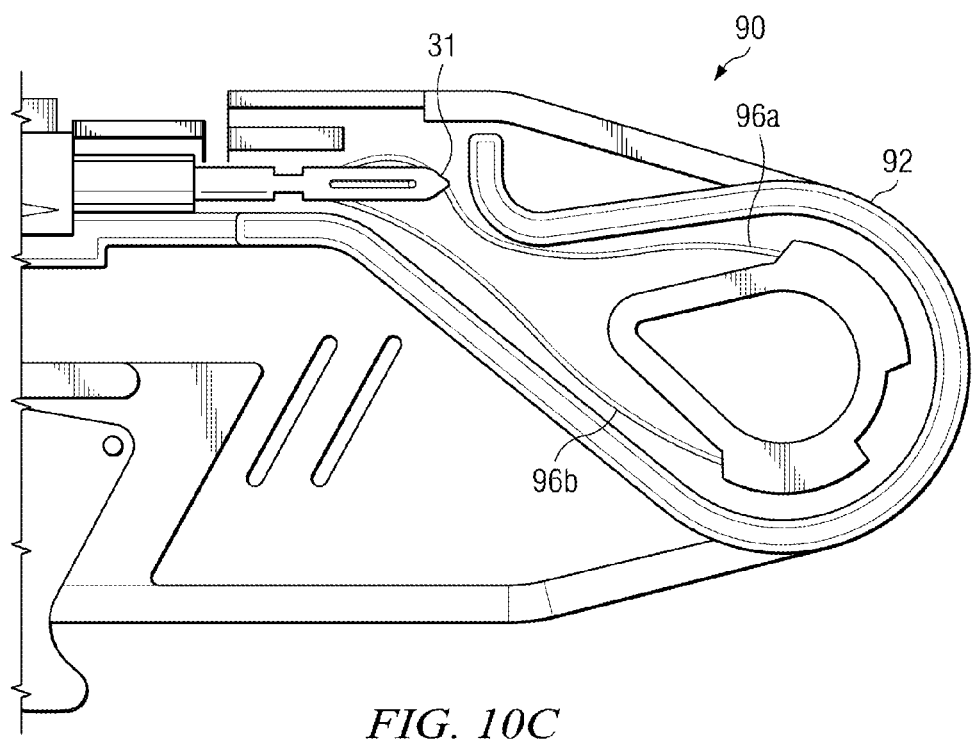

Now referring to FIGS. 10A to 10C, detail side views of suture loader 90 are illustrated showing examples of snaring mechanism and securing mechanism. As aforementioned, the suture loader 90 mechanism may be utilized with any of the bone anchoring instruments described herein for facilitating the loading of suture lengths through the one or more bone anchors and is not intended to be limiting. Suture loader 90 may be removably disposed at a distal end of outer tube 91 of a bone anchoring insertion instrument. Suture loader 90 may include suture guide 92 disposed at a distal end of loader 90 and in proximity to a bone anchor 31 disposed at the distal end of outer tube 91. Suture loader 90 may also include suture traps 93*a*, 93*b* and suture retaining members (or shutters)

94a, 94b. Traps 93a, 93b include apertures 88a, 88b (see FIG. 9B) and are located proximally from guide 92 and radially spaced from outer tube 91 in proximity to suture trap shutters 94a, 94b. Shutters 94a, 94b are pivotable in a generally radial direction with respect to outer tube 91 and may be configured to enclose traps 93a, 93b or to provide for a radial opening for traps 93a, 93b. Shutters 94a, 94b may be characterized by grooves 95a, 95b to help guide movement of the shutters.

Suture snares 96a, 96b may be provided and are preloaded within outer tube 91 and routed through the bone anchor 31 such that a free portion of snares 96a, 96b is exposed. A proximal portion of snares 96a, 96b may be retained on the tensioning mechanism of the bone anchor insertion device 30. Snares 96a, 96b may include snare ends 97a, 97b. Snare ends 97a, 97b may be characterized by apertures 98a, 98b and a plurality of teeth 99 located within apertures 98a, 98b. In a pre-snaring configuration, snares 96a, 96b are directed out from the bone anchor 31 and inserted into guide 92. Snare ends 97a, 97b are positioned within apertures 88a, 88b of traps 93a, 93b, respectively, and shutters 94a, 94b are positioned in an open configuration. Once a surgeon has placed a stitched loop of suture into a portion of soft tissue desired to be affixed near a bone surface, the separate free ends of suture, or suture limbs, may be respectively threaded into snare ends 97a, 97b and the shutters 94a, 94b may be pivoted to a closed configuration, thereby securing suture within snares 96a, 96b. In this configuration, the separate free ends of suture and the corresponding snare ends 97a, 97b are also secured with traps 93a, 93b such that the free ends do not drop out of position both within apertures 98a, 98b of snare ends 97a, 97b and with respect to the insertion instrument itself.

With the free ends of the suture and snare ends 97a, 97b secured in traps 93a, 93b, snares 96a, 96b may be withdrawn through the bone anchor 31 and into outer tube 91 by actuating the tensioning mechanism. As snare ends 97a, 97b and the free ends of the suture are drawn through traps 93a, 93b and shutters 94a, 94b, apertures 98a, 98b are compressed between the outer walls of traps 93a, 93b such that the plurality of teeth 99 on both snare ends 97a, 97b are compressed or bite into the corresponding free ends of suture. With the free ends of suture retained within snare ends 97a, 97b, snares 96a, 96b are drawn through suture loader 90 and into the bone anchor 31 and outer tube 91. Specifically, as the tensioning mechanism is actuated, snares 96a, 96b are routed through suture guide 92 and through the bone anchor and then into outer tube 91. Once snares 96a, 96b and the free ends of suture have been substantially withdrawn through the bone anchor 31 and into outer tube 91 to create a pre-tensioning configuration, suture loader 90 may be removed from outer tube 91. The separate free ends of suture are thereby engaged by the tensioning mechanism of the bone anchoring insertion instrument and may be independently tensioned as desired and described above.

Figure 11A:
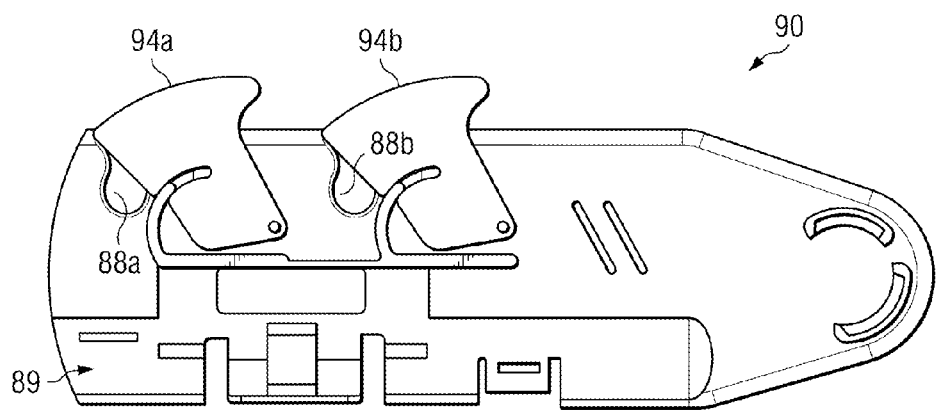
FIGS. 11A and 11B illustrate side views of a suture loader mechanism.
Figure 11B:
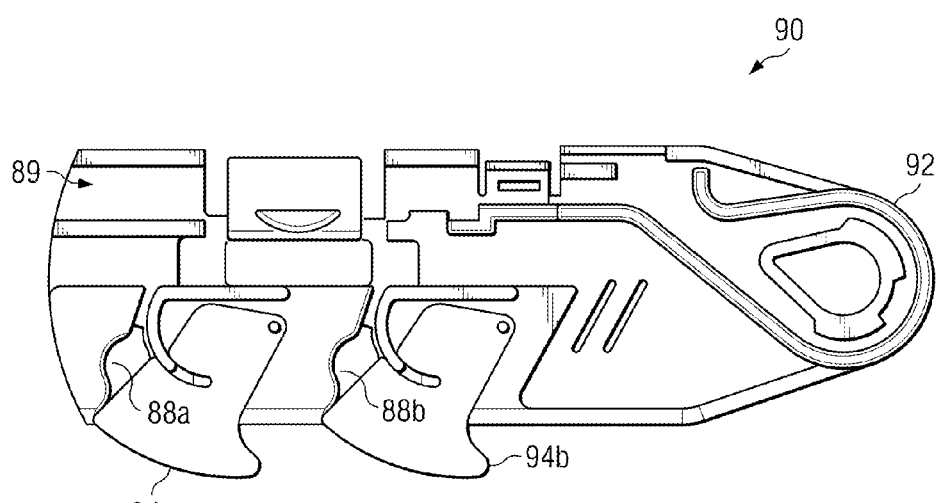
Figure 11C:
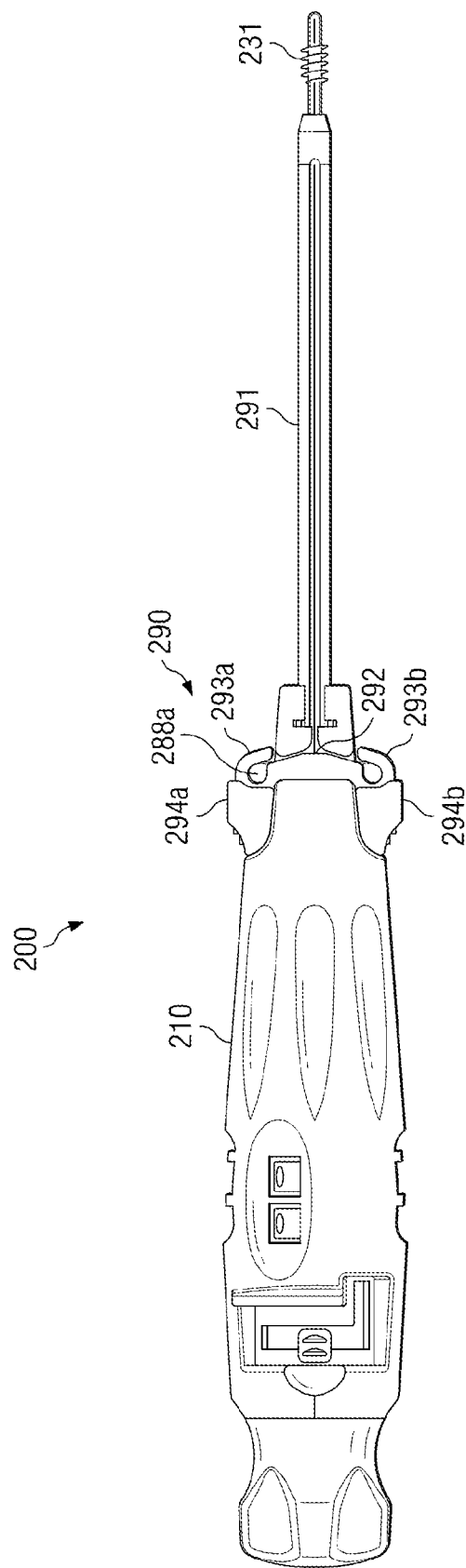
FIGS. 11C and 11D illustrate perspective views of an embodiment of a suture loader mechanism.
Figure 11D:
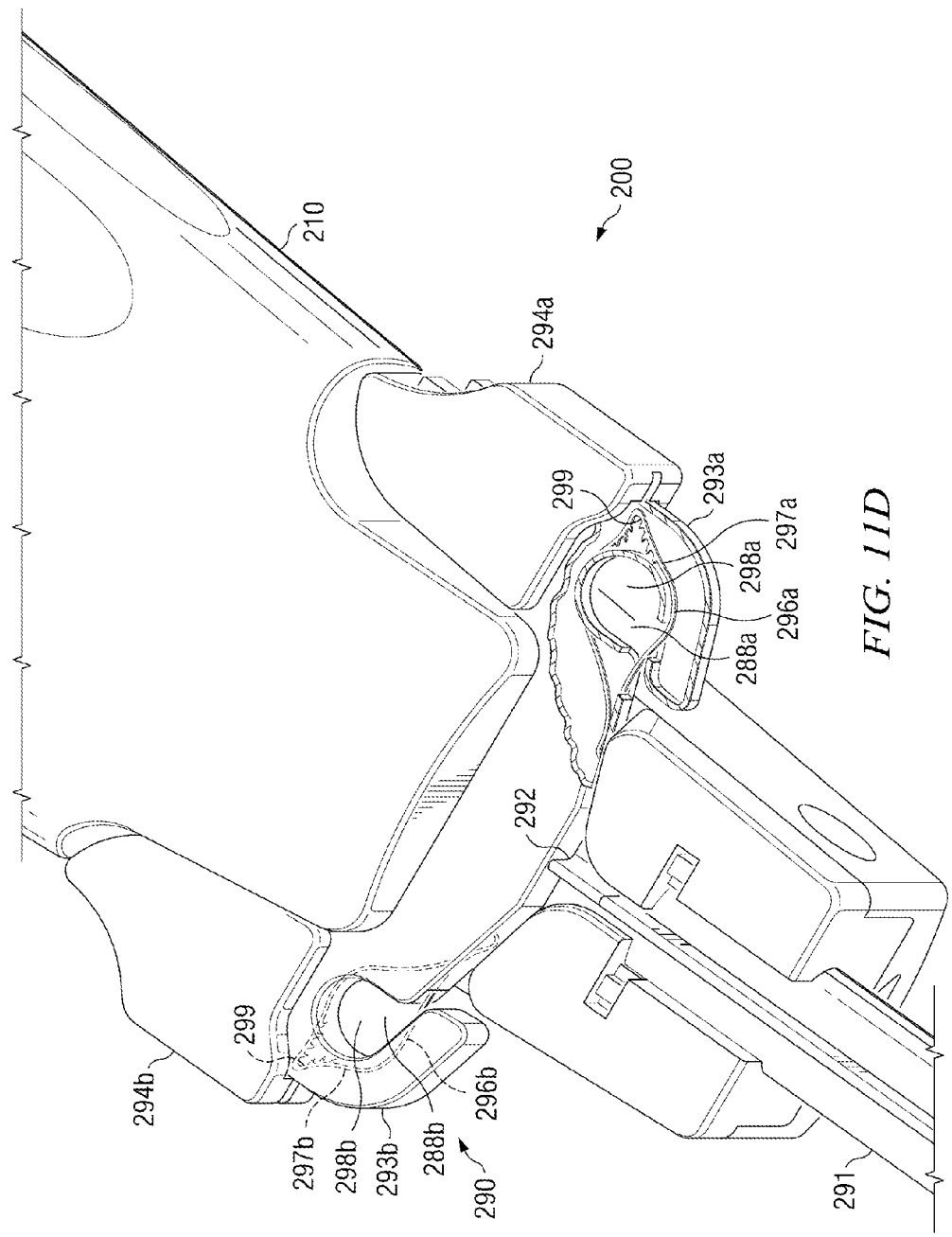

FIGS. 11A and 11B show respective side views of suture loader 90 illustrating details such as the suture guide 92 passage disposed distally from channel 89, as well as respective apertures 88a, 88b and corresponding shutters 94a, 94b spaced radially from channel 89. Referring now to FIGS. 11C and 11D, in certain embodiments the suture loader mechanism may be disposed at a more proximal location with respect to outer tube 291 of a bone anchoring insertion instrument 200. In these embodiments, suture loader 290 may include suture guide 292, suture traps 293a, 293b and suture retaining members 294a, 294b. Traps 293a, 293b include apertures 288a, 288b and are located adjacent to handle 210 in proximity to retaining members 294a, 294b. Retaining members 294a, 294b are slidable in a generally axially direction with respect to outer tube 291 and may be configured to enclose traps 293a, 293b or alternatively to provide for an opening through traps 293a, 293b and access to apertures 298a, 298b. Suture snares 296a, 296b may be provided and are preloaded within bone anchoring instrument 200 and routed through outer tube 291 and bone anchor 231 such that snare ends 297a, 297b are housed within suture traps 293a, 293b, respectively. Snare ends 297a, 297b may be characterized by snare apertures 298a, 298b and a plurality of teeth 299 located within apertures 298a, 298b.

The separate free ends from a stitched loop of suture may be respectively threaded into snare ends 297a, 297b and suture retaining members 294a, 294b may be slid to a closed configuration, thereby securing the suture free ends within snares 296a, 296b. Snares 296a, 296b may then be withdrawn into outer tube 291 through guide 292 such that apertures 298a, 298b are compressed, thereby resulting in the plurality of teeth on snare ends 297a, 297b compressing or biting into the corresponding free end of suture. With the free ends of suture secured within snare ends 297a, 297b, snare ends 297a, 297b are pulled in a generally distal direction through outer tube 291 and through bone anchor 231 by actuation of the tensioning mechanism, where snare ends 297a, 297b and the corresponding free ends of suture are routed through bone anchor 231 and then turned to be pulled back through outer tube 291 in a generally proximal direction toward handle 210. The free ends of suture ultimately engage the tensioning mechanism of the bone anchoring instrument and may then be independently tensioned as desired and as described above.

Figure 12A:
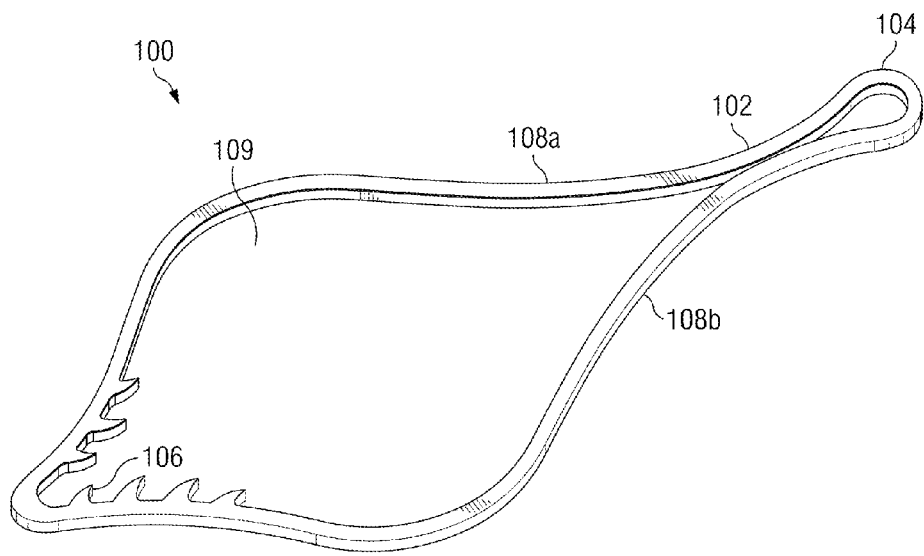
FIGS. 12A and 12B illustrate a perspective view of an embodiment of the suture snaring end portion.
Figure 12B:
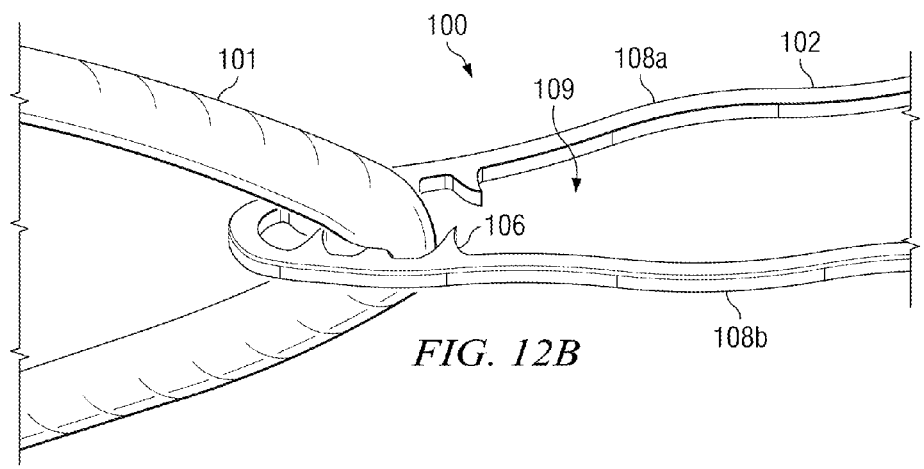

Referring now to FIGS. 12A and 12B, one embodiment of a snare end is shown. In certain embodiments, snare end 100 may include body 102 which defines a proximal loop 104 and which form arms 108a, 108b which extend distally to form aperture 109 as a closed loop. One or both arms 108a, 108b may further define suture securement members or projections, e.g., a plurality of teeth 106, which extend towards one another in apposition along opposing arms 108a, 108b and which are configured to interdigitate or close upon one another when snare end 100 is collapsed or urged into its low profile or closed configuration for snaring or securing a suture length. In certain embodiments, a length of material such as a polyester strand may be threaded through loop 104 and drawn through the bone anchor and attached to the tensioning mechanism.

Now referring to FIG. 12B, after a strand of suture 101 is threaded through aperture 109, which is positioned within aperture 98a and/or 98b of suture loader 90 as described above, snare end 100 is compressed such that arms 108a, 108b are pushed toward one another, thereby closing aperture 109 and causing the plurality of teeth 106 to engage the strand of suture 101. In certain embodiments, the compression of snare end 100 takes place as snare end 100 is withdrawn through a suture loader 90, as described above. The plurality of teeth 106 of suture end 100 compress or bite into the strand of suture 101, resulting in a resistance to the strand of suture 101 pulling out of aperture 109 when placed under tensile load.

Figure 13:
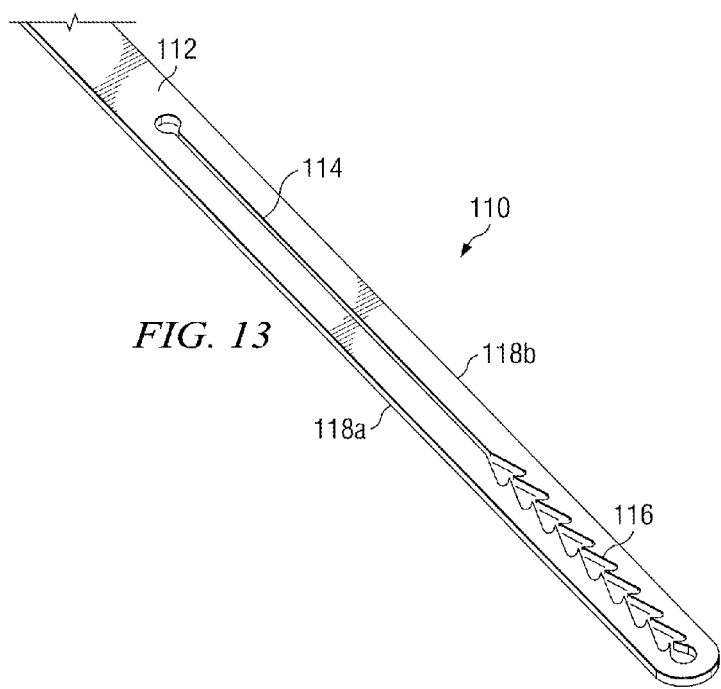
FIGS. 13 and 14 illustrate a perspective view of an additional embodiment of the suture snaring end portion.
Figure 14:
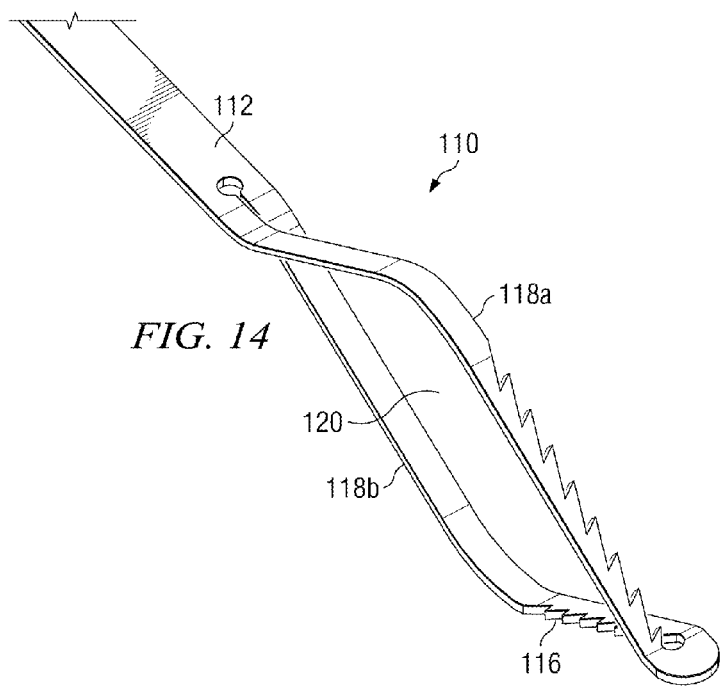

Referring now to FIGS. 13 and 14, an additional embodiment of a snare end is shown. Snare end 110 may include body 112, slit 114, and plurality of teeth 116. Arms 118a, 118b are formed on either side of slit 114. In certain embodiments, body 112 is also part of a length of material included with the larger snare which is routed through the bone anchor and attached to the tensioning mechanism. Snare end 110 is preferably fabricated from stainless steel by laser cutting, but may be fabricated from many different materials (e.g., carbon steel or beryllium copper) and by various methods (e.g., photochemical etching, stamping or wire EDM). Referring now to FIG. 14, snare end 110 has been configured to accept a strand of suture where arms 118a, 118b have been deflected to create aperture 120, which is capable of receiving a strand of suture. In this variation, arms 118a, 118b may be urged or formed to configure into an expanded profile by bending or curving out-of-plane in opposing directions relative to a proximal end of body 112. After a strand of suture is threaded through aperture 120, snare end 110 is reformed to the configuration shown in FIG. 13 such that the strand of suture is captured by plurality of teeth 116 in a shearing type action. In certain embodiments, the reformation of snare end 110 takes place as snare end 110 is withdrawn through a suture loader, as described above. The plurality of teeth 116 of suture end 110 compress or bite into the strand of suture, resulting in a resistance to the strand of suture pulling out of aperture 120 when placed under tensile load.

Generally, the suture snares described herein may be utilized in conjunction with any of the suture loader embodiments described above. Alternatively, in certain embodiments the suture snares 100 or 110 described above may be used independently of a suture loader. In these embodiments, the suture snare is preferably drawn through the bone anchor disposed at the distal end of the bone anchoring instrument, such that the bone anchor compresses the suture snare with a free end of suture disposed therein thereby closing the aperture of the suture snare and causing the plurality of teeth to engage or bite into the free end of suture.

While preferred embodiments of this invention have been shown and described, modifications thereof can be made by one skilled in the art without departing from the scope or teaching herein. The embodiments described herein are exemplary only and are not limiting. Because many varying and different embodiments may be made within the scope of the present teachings, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. A method for tensioning suture, comprising:
   tensioning a first suture length coupled to a first tensioning member and a second suture length coupled to a second tensioning member by rotating the first and second tensioning members which are each positioned within or along a handle;
   repositioning a tensioning selector to a first position such that the first and second tensioning members are disengaged from one another; and
   further tensioning the first suture length by rotating the first tensioning member independently of the second tensioning member.

2. The method of claim 1 further comprising:
   passing said first and second suture lengths through a portion of soft tissue;
   passing said first and second suture lengths through one or more bone anchors;
   deploying the one or more bone anchors through the portion of soft tissue and into an underlying portion of adjacent bone prior to tensioning; and
   approximating the portion of soft tissue to the portion of adjacent bone.

3. The method of claim 1 wherein tensioning further comprises simultaneously tensioning the first and second suture lengths.

4. The method of claim 1 wherein tensioning further comprises constraining rotation of the first and second tensioning members to rotate in a first direction while inhibiting rotation in a second opposite direction.

5. The method of claim 1 wherein repositioning comprises moving the selector from a neutral position where the first and second tensioning members are engaged to one another.

6. The method of claim 1 further comprising:
   repositioning the selector to a second position such that the second tensioning member is rotatable independently of the first tensioning member; and
   further tensioning the second suture length by rotating the second tensioning member independently of the first tensioning member.

* * * * *